United States Patent
Goto et al.

(10) Patent No.: US 9,481,638 B2
(45) Date of Patent: Nov. 1, 2016

(54) SCANDIUM EXTRACTION METHOD

(71) Applicants: Kyushu University, National University Corporation, Fukuoka-shi, Fukuoka (JP); SUMITOMO METAL MINING CO., LTD., Tokyo (JP)

(72) Inventors: Masahiro Goto, Fukuoka (JP); Fukiko Kubota, Fukuoka (JP); Yuzo Baba, Fukuoka (JP)

(73) Assignees: Kyushu University, National University Corporation, Fukuoka-shi (JP); SUMITOMO METAL MINING CO., LTD., Tokyo (JP)

( * ) Notice: Subject to any disclaimer, the term of this patent is extended or adjusted under 35 U.S.C. 154(b) by 0 days.

(21) Appl. No.: 14/130,283

(22) PCT Filed: Feb. 21, 2013

(86) PCT No.: PCT/JP2013/054419
§ 371 (c)(1),
(2) Date: Dec. 30, 2013

(87) PCT Pub. No.: WO2013/136941
PCT Pub. Date: Sep. 19, 2013

(65) Prior Publication Data
US 2014/0377150 A1    Dec. 25, 2014

(30) Foreign Application Priority Data
Mar. 13, 2012 (JP) .................... 2012-056134

(51) Int. Cl.
| | |
|---|---|
| C22B 3/00 | (2006.01) |
| C07C 237/06 | (2006.01) |
| C22B 3/28 | (2006.01) |
| C22B 3/26 | (2006.01) |
| C22B 3/32 | (2006.01) |
| C22B 59/00 | (2006.01) |

(52) U.S. Cl.
CPC ............ *C07C 237/06* (2013.01); *C22B 3/001* (2013.01); *C22B 3/0005* (2013.01); *C22B 3/0024* (2013.01); *C22B 3/0032* (2013.01); *C22B 59/00* (2013.01)

(58) Field of Classification Search
None
See application file for complete search history.

(56) References Cited

U.S. PATENT DOCUMENTS

| | | |
|---|---|---|
| 6,267,936 B1 | 7/2001 | Delmas et al. |
| 8,951,486 B2 | 2/2015 | Goto et al. |
| 9,011,804 B2 | 4/2015 | Goto et al. |
| 2005/0124765 A1 | 6/2005 | Seko et al. |
| 2013/0102806 A1 | 4/2013 | Sakaki et al. |
| 2014/0234187 A1* | 8/2014 | Goto et al. ............ 423/21.5 |
| 2014/0328737 A1* | 11/2014 | Goto et al. ............ 423/139 |
| 2015/0315674 A1 | 11/2015 | Goto et al. |

FOREIGN PATENT DOCUMENTS

| | | | |
|---|---|---|---|
| AU | 725800 B2 | | 10/2000 |
| CN | 101519427 A | | 9/2009 |
| CN | 103582711 | | 2/2014 |
| CN | 104822851 | A | 8/2015 |
| EP | 0834581 | A1 | 4/1998 |
| EP | 2679693 | A1 | 1/2014 |
| EP | 2682486 | A1 | 1/2014 |
| EP | 2712940 | A1 | 4/2014 |
| JP | 4-074711 | A | 3/1992 |
| JP | 09-143589 | A | 6/1997 |
| JP | H-09-291320 | A | 11/1997 |
| JP | 2000-212658 | A | 8/2000 |
| JP | 2000-234130 | A | 8/2000 |
| JP | 2000313928 | A | 11/2000 |
| JP | 2007-327085 | A | 12/2007 |
| JP | 2009-256291 | A | 11/2009 |
| JP | 2010-174366 | A | 8/2010 |
| JP | 2012-102062 | A | 5/2012 |
| JP | 2013-216656 | A | 10/2013 |

(Continued)

OTHER PUBLICATIONS

Machine Translation of Office action issued in CN App. No. 201380002904.1, mailed Jun. 26, 2015.*
Extended European Search Report for EP Appln. No. 13761717.1 dated Oct. 14, 2014.
Yuzo, Baba et al; "Development of Novel Extractants with Amino Acid Structure for Efficient Separation of Nickel and Cobalt from Manganese Ions", Industrial & Engineering Chemistry Research; vol. 53, No. 2, Dec. 25, 2013; pp. 812-818.
Smith, B.F., et al; "Amides as Phase Modifiers for N,N'-Tetraalkylmalonamide Extraction of Actinides and Lanthanides From Nitric Acid Solutions"; Separation Science and Technology; vol. 32, Jan. 1, 1997; pp. 149-173.

(Continued)

*Primary Examiner* — Steven Bos
(74) *Attorney, Agent, or Firm* — Locke Lord LLP

(57) ABSTRACT

Provided is a method for selectively extracting and inexpensively recovering scandium from an acidic solution containing calcium, magnesium, and scandium. The scandium extraction method according to the present invention involves subjecting an acidic solution containing calcium, magnesium, and scandium to solvent extraction using an extraction agent consisting of an amide derivative represented by the general formula below. In the formula, $R^1$ and $R^2$ represent the same or different alkyl groups, and $R^3$ is a hydrogen atom or alkyl group. The amide derivative preferably consisting of one or more derivatives selected from glycine amide derivatives, histidine amide derivatives, lysine amide derivatives, and aspartic acid amide derivatives. The pH of the acidic solution is preferably pre-adjusted to between 1 and 4.

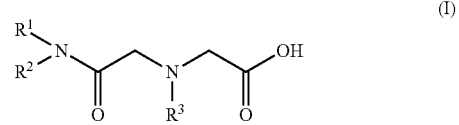

(I)

5 Claims, 2 Drawing Sheets

(56) References Cited

FOREIGN PATENT DOCUMENTS

| WO | WO-2012005183 A1 | 1/2012 |
|---|---|---|
| WO | WO-2013/069562 A1 | 5/2013 |
| WO | WO-2013/069563 A1 | 5/2013 |
| WO | WO-2014/148431 A1 | 9/2014 |

OTHER PUBLICATIONS

International Search Report of PCT/JP2013/054419.
Office Action issued to CN Application No. 201380002904.1, mailed Jun. 26, 2015.
Pajewski, Robert et al; "The effect of midpolar regime mimics on anion transport mediated by amphiphilic heptapeptides", New Journal of Chemistry, 2007, 31, 1960-1972.
K. Shimojo et al., "Extraction behavior and separation of lanthanides with a diglycol amic acid derivative and a nitrogen-donor ligand," Anal. Sci., 23, Dec. 2007, pp. 1427-1430.
Hirofumi Morizono et al., "Liquid-liquid extraction of transition metal ions with an alkylhistidine extractant," Separation and Purification Technology, vol. 80 No. 2, Elsevier B.V., Jul. 29, 2011, pp. 390-395.
Office Action for Japanese Patent Application No. 2013-084951 dated Jan. 14, 2014.
CAS Registration No. 1156229-80-9.
Extended European search report for European Patent Application No. 12848105.8 dated Jan. 22, 2014.
Naganawa H et al: "A New "Green" Extractant of the Diglycol Amic Acid Type for Lanthanides", Solvent Extraction Research and Development, Japan, Japanese Association of Solvent Extraction, Saga, JP, vol. 14, Jan. 1, 2007, pp. 151-159.
Singh D K et al: "Extraction of rare earths and yttrium with high molecular weight carboxylic acids," Hydrometallurgy, Elsevier Scientific Publishing CY. Amsterdam, NL, vol. 81, No. 3-4, Mar. 1, 2006, pp. 174-181.
Extended European search report for European Patent Application No. 12847107.5 dated Feb. 6, 2014.
Holger Stephan et al: "Liquid-Liquid Extraction of Metal Ions with Amido Podands", Solvent Extraction and Ion Exchange, Taylor & Francis Group LLC, US, vol. 9, No. 3, Jan. 1, 1991, pp. 459-469.
Office Action for Japanese Patent Application No. 2014-022868 dated Apr. 8, 2014.
CAS Registration No. 1153237-54-7.
CAS Registration No. 1153399-39-3.
CAS Registration No. 1178468-85-3.
CAS Registration No. 1179174-30-1.
CAS Registration No. 1182789-10-1.
CAS Registration No. 1183588-00-2.
CAS Registration No. 1291231-35-0.
Extended European search report for European Patent Application No. 14770382.1 dated Feb. 16, 2016.
Office Action for Chinese Patent Application No. 201480008628.4 dated Mar. 10, 2016.
Office Action for U.S. Appl. No. 14/765,307 dated Apr. 6, 2016.
Office Action dated Jul. 15, 2015, issued for U.S. Appl. No. 14/423,061.
Office Action dated Nov. 23, 2015, issued for CN Application No. 201380042793.7.

* cited by examiner

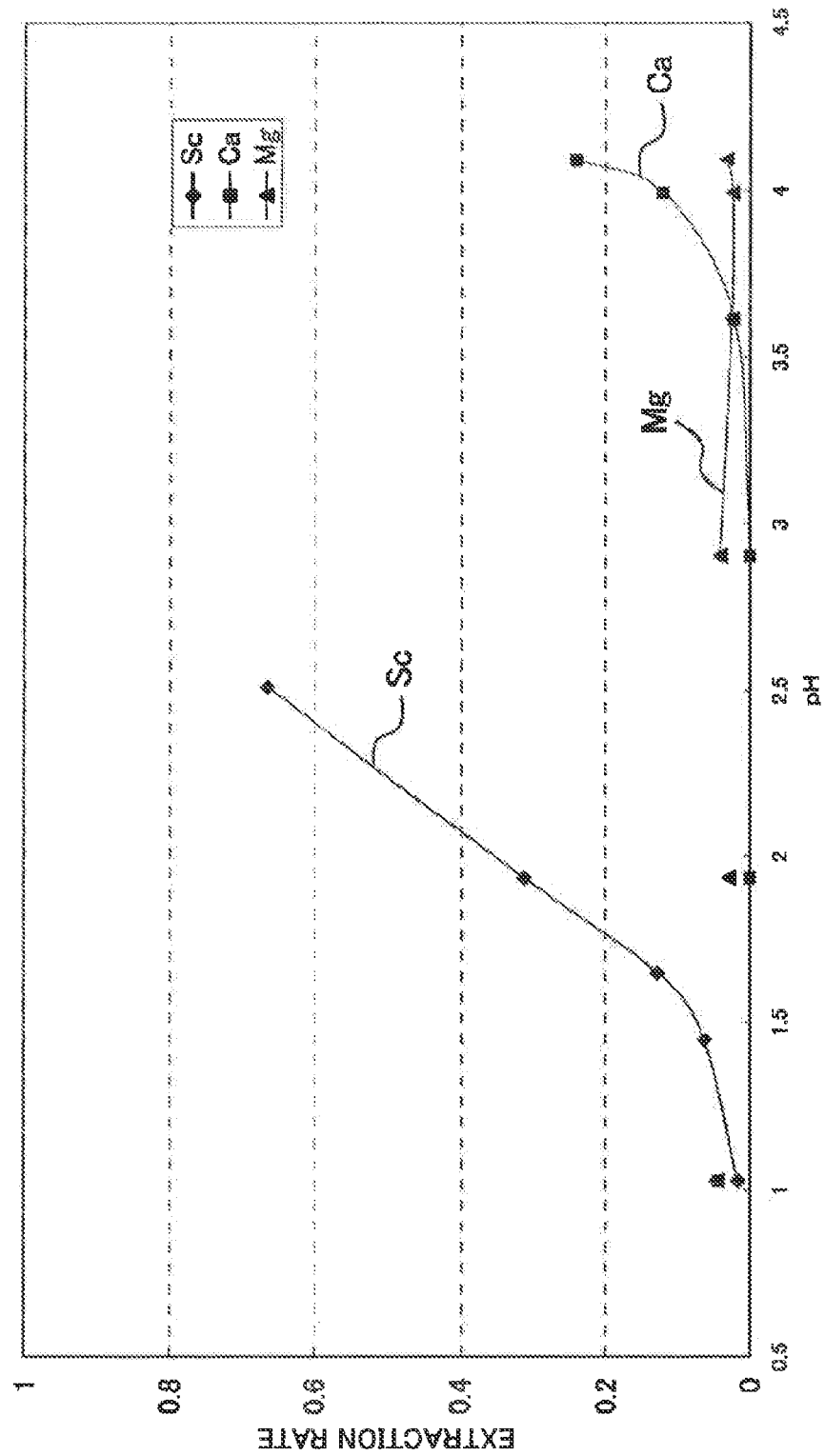

SCANDIUM EXTRACTION METHOD

CROSS-REFERENCE TO RELATED APPLICATIONS

This application is the national phase under 35 U.S.C. §371 of PCT International Application No. PCT/JP2013/054419, filed Feb. 21, 2013, which claims the benefit of Japanese Patent Application No. 2012-056134, filed Mar. 13, 2012, the entire contents of the aforementioned applications are hereby incorporated herein by reference.

TECHNICAL FIELD

The present invention relates to a scandium extraction method and, in detail, relates to a method of efficiently separating and extracting scandium from an acidic solution containing calcium, magnesium and scandium.

BACKGROUND ART

Scandium, which has the smallest atomic number among the rare earth elements, has been used as a material for metal halide lamps, an added element in alloys, an added element in catalyst ceramics, and the like. However, scandium is expensive, the output thereof is limited, and separation and refinement are difficult, and thus the application of scandium has been limited.

However, nickel oxide ore such as laterite ore has been known to contain very small amounts of scandium. The scandium contained in nickel oxide ore can be recovered from the leachate obtained by adding sulfuric acid to the nickel oxide ore and pressurized extracting.

For example, Patent Document 1 shows that it is possible to recover nickel and scandium from oxide ores by performing: (A) a leaching step of leaching the oxide ore with an acid under high temperature and high pressure to obtain a leachate containing nickel and scandium; (B) a first neutralizing step of removing iron and aluminum in the leachate as precipitates by adjusting the pH to the range of 2 to 4 by adding a neutralizing agent to this leachate; (C) a second neutralizing step of recovering scandium in the solution as a precipitate by adjusting the pH to more than 4 to 7.5 by adding a neutralizing agent to the solution after removing the precipitates in the first neutralizing step; and (D) a third neutralizing step of recovering nickel in the solution as a precipitate by adjusting the pH to more than 7.5 by further adding neutralizing agent.

However, various problems arise when trying to industrially operate with the method described in Patent Document 1. For example, since the pH adjustment range in the first neutralizing step and the pH adjustment range in the second neutralizing step are adjacent, there is a possibility of scandium also precipitating along with iron and aluminum in the first neutralizing step, leading to an extraction rate decline for scandium, and there is a possibility of iron and aluminum precipitating along with scandium in the second neutralizing step, leading to a purity decline for scandium, and neither are preferable. In addition, although large amounts of precipitates are generated by adding a neutralizing agent, in general, the characteristics of the precipitates obtained by adding an alkali to an acid are unstable and poor in filterability, and there is a possibility of being accompanied with a cost increase such as the enlargement of the equipment scale. For this reason, it is preferable to decrease the number of times of the neutralizing step as much as possible, and it has been proposed to selectively separate only scandium by a means such as solvent extraction from a solution containing scandium.

Patent Document 2 shows that high purity scandium oxide is obtained by extracting scandium component into organic solvent by adding the organic solvent to an aqueous-phase scandium-containing solution containing, in addition to scandium, at least one among iron, aluminum, calcium, yttrium, manganese, chromium and magnesium, then in order to separate trace components extracted along with scandium in the organic solvent, scrubbing is performed by adding a hydrochloric acid aqueous solution, and after removing the trace components, the scandium remaining in the organic solvent is made into a slurry containing as $Sc(OH)_3$ by adding a sodium hydroxide aqueous solution to the organic solvent, the $Sc(OH)_3$ obtained by filtering this is dissolved with hydrochloric acid to obtain a scandium chloride aqueous solution, and scandium oxalic acid precipitate is formed by adding to this oxalic acid, the precipitate is filtered, and after separating the trace impurities in the filtrate, calcining.

However, in the case of employing the method of Patent Document 2, not only scandium, but also impurity components are extracted in the organic solvent to an extent that cannot be ignored. Calcium, magnesium, etc. are abundantly present particularly in the leachate obtained by acid leaching and neutralizing nickel oxide ore, and for this reason, in addition to the problem of labor and cost required in scrubbing, there is also a further problem in the treatment of drainage generated accompanying scrubbing.

In addition, Patent Document 3 discloses an extraction agent called DODGAA, which has a diglycol amic acid backbone. According to this extraction agent, the solubility in water is extremely small, and as well as complete incineration being possible, comparing with existing phosphorous-based compounds, it has superior rare earth metal extractability and selective separability, as well as the synthesis cost being low.

However, since scandium is very sensitive to pH, upon extracting scandium even with the above-mentioned extraction agent shown in Patent Document 3, a practical extraction rate is not obtained if maintaining the pH at a constant or higher. Moreover, in the pH range suited to the extraction of scandium, the extraction rate of not only scandium, but also calcium and magnesium increase, and thus it is difficult to selectively separate only scandium.

[Patent Document 1] Japanese Unexamined Patent Application, Publication No. 2000-313928
[Patent Document 2] Japanese Unexamined Patent Application, Publication No. H9-291320
[Patent Document 3] Japanese Unexamined Patent Application, Publication No. 2007-327085

DISCLOSURE OF THE INVENTION

Problems to be Solved by the Invention

The present invention aims to provide a method for selectively extracting and inexpensively recovering scandium from an acidic solution containing calcium, magnesium and scandium.

The present inventors have thoroughly researched to solve the above-mentioned problems, and found that the above-mentioned object can be achieved by solvent extracting using an extraction agent consisting of an amide or an amide derivative, thereby arriving at completion of the present invention.

Means for Solving the Problems

More specifically, the present invention provides the following.

A first aspect of the present invention is a scandium extraction method that includes: subjecting an acidic solution containing calcium, magnesium and scandium to solvent extraction by way of an extraction agent consisting of an amide derivative represented by the following general formula (I).

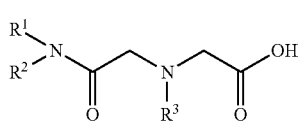

(I)

(In the formula, R1 and R2 each represent the same or different alkyl groups. The alkyl group may be either linear or a branched chain. R3 represents a hydrogen atom or alkyl group.)

In addition, according to a second aspect of the present invention, in the scandium extraction method as described in the first aspect, the amide derivative is at least any one of a glycine amide derivative, histidine amide derivative, lysine amide derivative and aspartic acid amide derivative.

Furthermore, according to a third aspect of the present invention, in the scandium extraction method as described in the first or second aspect, the acidic solution is subjected to the solvent extraction while adjusting the pH of the acidic solution to the range of 1 to 4.

Moreover, according to a fourth aspect of the present invention, in the scandium extraction method as described in any one of the first to third aspects, the acidic solution is a solution formed by mixing sulfuric acid with nickel oxide ore to leach out nickel.

Effects of the Invention

According to the present invention, since it is possible to extract scandium with a high recovery rate even in a low pH range, calcium and magnesium can be efficiently separated, contrary to convention extraction agents. In addition, the number of extraction stages in actual operation is few, and thus the equipment scale can be condensed; therefore, scandium can be recovered inexpensively.

BRIEF DESCRIPTION OF THE DRAWINGS

FIG. 2 shows the results when extracting scandium from an acidic solution containing calcium, magnesium and scandium, using an extraction agent of a comparative example.

PREFERRED MODE FOR CARRYING OUT THE INVENTION

Figure 1:
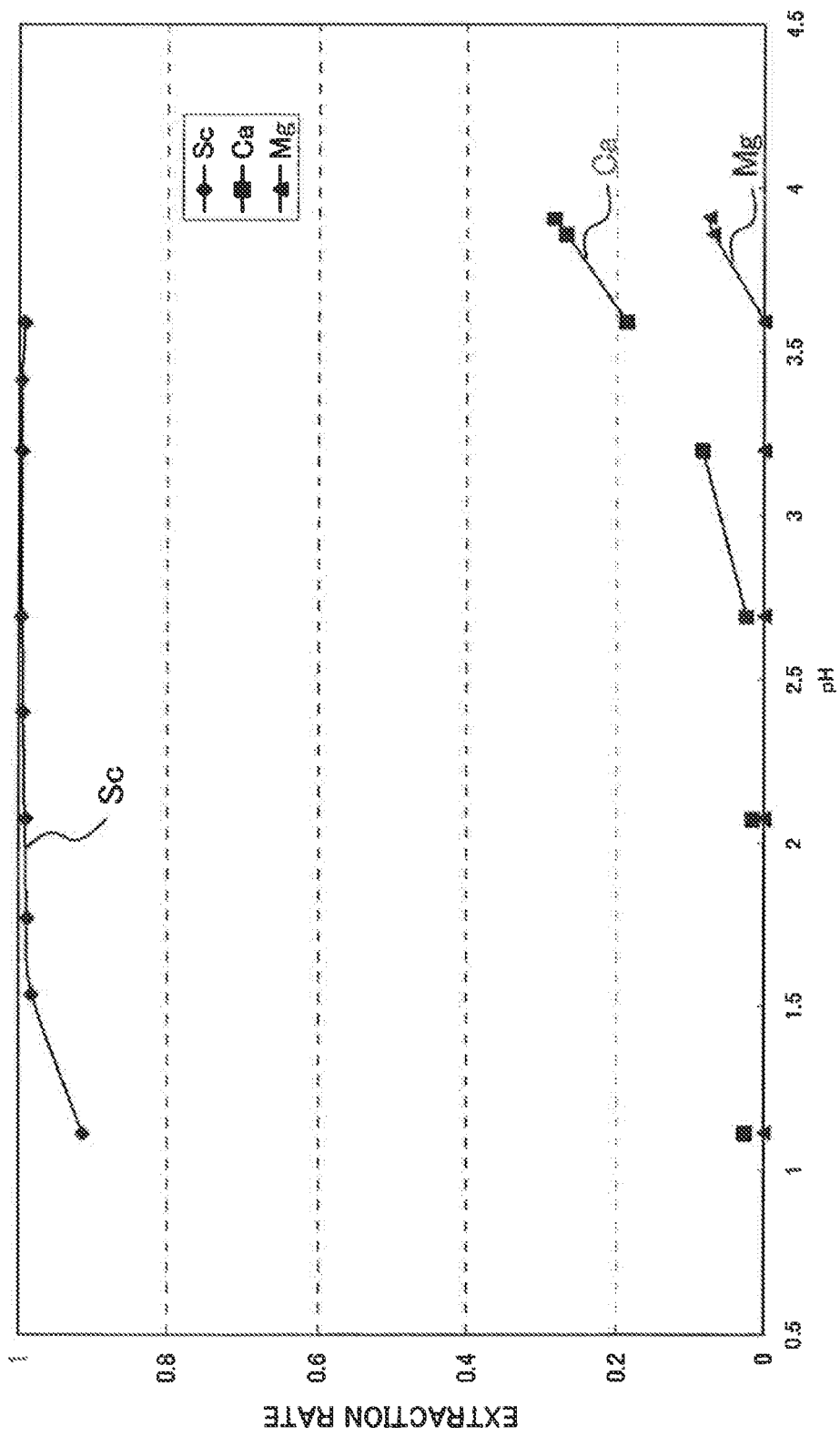
FIG. 1 shows the results when extracting scandium from an acidic solution containing calcium, magnesium and scandium, using an extraction agent of an example.

Although specific embodiments of the present invention will be explained in detail hereinafter, the present invention is in no way limited to the following embodiments, and can be implemented by adding appropriate modifications within the scope of the object of the present invention.

The present invention subjects an acidic solution containing calcium, magnesium and scandium to solvent extraction by way of an extraction agent consisting of an amide or amide derivative, and extracts the above-mentioned scandium from the above-mentioned acidic solution.

Extraction Solvent

The extraction agent consists of an amide derivative represented by the following general formula (I).

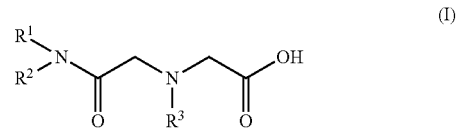

(I)

In the formula, substituents $R^1$ and $R^2$ indicate the same or different alkyl groups. The alkyl group may be linear or branched chains. $R^3$ indicates a hydrogen atom or an alkyl group. With the present invention, by introducing an alkyl group to the backbone of the amide, it is possible to raise the lipophilicity and use as an extraction agent.

The above-mentioned amide derivative is at least any one of a glycine amide derivative, histidine amide derivative, lysine amide derivative and aspartic acid amide derivative. In the case of the amide derivative being a glycine amide derivative, the above-mentioned glycine amide derivative can be synthesized by the following method. First, 2-halogenated acetyl halide is added to an alkyl amine of a structure represented by $NHR^1R^2$ ($R^1$ and $R^2$ are the same as the above-mentioned substituents $R^1$ and $R^2$), and a hydrogen atom of amine is substituted with the 2-halogenated acetyl by way of nucleophilic substitution reaction, thereby obtaining a 2-halogenated (N,N-di)alkyl acetamide.

Next, the above-mentioned 2-halogenated (N,N-di)alkyl acetamide is added to a glycine or N-alkylglycine derivative, and one of the hydrogen atoms of the glycine or N-alkylglycine derivative is substituted with (N,N-di)alkyl acetamide by way of nucleophilic substitution reaction. The glycine alkyl amide derivative can be synthesized by these two stages of reaction.

It should be noted that, if glycine is replaced with histidine, lysine or aspartic acid, it is possible to synthesize a histidine amide derivative, lysine amide derivative or aspartic acid amide derivative.

Extraction of Scandium

To extract scandium ions using an extraction agent synthesized by the above-mentioned method, an acidic aqueous solution containing the target scandium ions is adjusted, while adding and mixing this acidic aqueous solution to an organic solution of the above-mentioned extraction agent. It is thereby possible to selectively extract the target scandium ions in the organic phase.

The organic solvent after extracting scandium ions was isolated, and to this was added a back extraction starting liquid for which the pH had been adjusted to be lower than the above-mentioned acidic aqueous solution and stirred, thereby extracting and separating the target scandium ions from the organic solvent, and further, the target scandium ions could be recovered in an aqueous solution by back extracting the target scandium ions from the organic solvent. As a back extraction solution, for example, an aqueous solution in which nitric acid, hydrochloric acid or sulfuric acid is diluted is favorably used. In addition, by appropriately changing the ratio of organic phase to aqueous phase, the scandium ions can be concentrated.

The organic solvent may be any kind so long as being a solvent in which the extraction agent and metal extracted species dissolve, and for example, chlorinated solvents such as chloroform and dichloromethane:aromatic hydrocarbons such as benzene, toluene and xylene; aliphatic hydrocarbons such as hexane; etc. can be exemplified. These organic solvents can be used individually, or two or more organic solvents can be mixed, and alcohols such as 1-octanol can be mixed therewith.

The concentration of the extraction agent can be set as appropriate according to the concentration of scandium. In addition, the stirring time and extraction temperature may be appropriately set according to the requirements of the acidic aqueous solution of scandium ions and the organic solution of extraction agent.

In order to efficiently recover scandium from an acidic aqueous solution containing calcium, magnesium and scandium, it is preferable to add the organic solution of extraction agent while adjusting the pH of the acidic aqueous solution containing calcium, magnesium and scandium to at least 1 and no more than 4, and it is more preferable to add the organic solution of extraction agent while adjusting the above-mentioned pH to at least 1.5 and no more than 3.5. Since there is a possibility of not being able to sufficiently extract scandium if the pH is less than 1, it is not preferable. Since not only scandium, but also calcium and magnesium will be extracted if the pH exceeds 4, it is not preferable.

EXAMPLES

Hereinafter, the present invention will be explained in further detail by way of the Examples; however, the present invention is not subjected to any limitations in the following description.

Example

Synthesis of D2EHAG

As one example of the scandium extraction agent consisting of an amide or amide derivative, a glycine amide derivative represented by the following general formula (I), i.e. N,N-di(2-ethylhexyl)acetamide-2-glycine to which, two 2-ethylhexyl groups were introduced (N,N-di(2-ethylhexyl) acetamic-2-glycine is hereinafter referred to as "D2EHAG"), was synthesized.

The synthesis of D2EHAG was carried out in the following way. First, as shown in the following reaction formula (II), 2.41 g of commercially available di(2-ethylhexyl)amine (0.1 mol) and 1.01 g of triethyl amine (0.1 mol) were isolated, dissolved by adding chloroform to this, then in succession stirred while maintaining at a temperature in an ice bath, and 13.5 g of 2-chloroacetyl chloride (0.12 mol) was slowly added by dropping. After adding by dropping completed, it was stirred for 3 hours at room temperature. After stirring completed, it was washed once with 1 mol/L hydrochloric acid, subsequently washed several times with ion exchange water, and then the chloroform phase was isolated.

Next, anhydrous sodium sulfate was added in the appropriate amount (about 10 to 20 g), and after evaporating, was filtered under reduced pressure, and the solvent was distilled in an evaporator, thereby obtaining 29.1 g of yellow liquid. The structure of this yellow liquid (reaction product) was identified using a nuclear magnetic resonance instrument (NMR), upon which the above-mentioned yellow liquid was confirmed as being 2-chloro-N,N-di(2-ethylhexyl)acetamide (hereinafter referred to as "CDEHAA"). It should be noted that the yield of CDEHAA was 85% relative to di(2-ethylhexyl)amine, which was the source material.

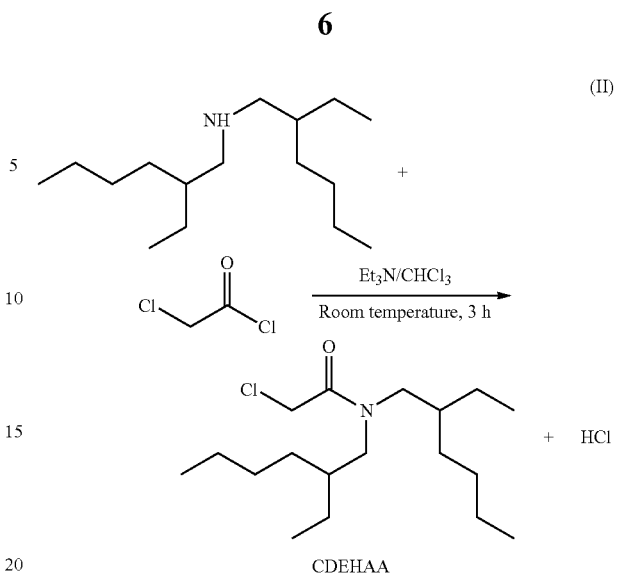

Next, as shown in the below reaction formula (III), while stirring at room temperature a solution arrived at by adding methanol to dissolve 8.0 g of sodium hydroxide (0.2 mol), and further adding 15.01 g of glycine (0.2 mol), 12.72 g of the above-mentioned CDEHAA (0.04 mol) was slowly added by dropping. After adding by dropping completed, it was stirred for 15 hours while maintaining at 60° C. After stirring was finished, the solvent in the reaction liquid was distilled using an evaporator, and chloroform was added to the residue to dissolve. After adding sulfuric acid to this solution to make acidic with a pH of about 1 to 5, it was washed several times with ion exchange water, and the chloroform was isolated.

An appropriate amount of anhydrous magnesium sulfate was added to dehydrate this chloroform phase, and was filtered. The solvent was removed under reduced pressure again to obtain 12.5 g of yellow paste. The yield based on the amount of the above-mentioned CDEHAA was 87%. The structure of the yellow paste was identified by NMR and elemental analysis, upon which it was confirmed to be D2EHAG. The extraction agent of the Example was obtained through the above-mentioned process.

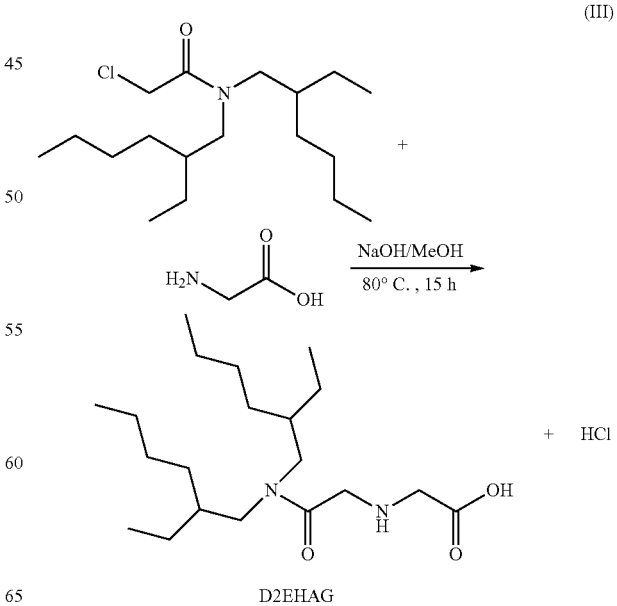

(Extraction of Scandium)

Using the above-mentioned extraction agent, extraction separation of scandium was carried out. The composition of the source liquid was 4.5 mg/l of scandium, 2.4 mg/l of magnesium and 4.0 mg/l of calcium.

The above-mentioned source liquid was isolated 3 ml at a time, a n-dodecane solution containing various types of sulfuric acid acidic solutions for which the pH was adjusted to 1.0 to 4.0 by adding sulfuric acid to this, and 0.01 mol/L extraction agent in the same volume (3 ml) as this was added to a test tube, placed inside a constant temperature storeroom at 25° C. and shaken for 24 hours. At this time, the pH of the sulfuric acidic solution was adjusted using ammonium nitrate, ammonia and nitric acid with a concentration of 1 mol/L.

After shaking, the aqueous phase was isolated, and the scandium concentration, calcium concentration and magnesium concentration were measured using ICP-AES. In addition, the organic phase was back extracted using 2 mol/L nitric acid. Then, the scandium concentration, calcium concentration and magnesium concentration in the back extract phase were measured using ICP-AES. From these measurement results, the extraction rates of scandium, calcium and magnesium were obtained, defining in amount of material in organic phase/(amount of material in organic phase+amount of material in aqueous phase). These results are shown in FIG. 1. The horizontal axis in FIG. 1 is the pH of the sulfuric acid acidic solution, and the vertical axis is the extraction rate of scandium, calcium or magnesium. In the graph, the diamonds indicate the extraction rate of scandium, the squares indicate the extraction rate of calcium, and the triangles indicate the extraction rate of magnesium.

Comparative Example

Synthesis of DODGAA

N,N-dioctyl-3-oxapentane-1,5-amic acid (hereinafter referred to as "DODGAA"), which is a conventional, known rare earth metal extraction agent, was used as the extraction agent of the Comparative Example.

The synthesis of DODGAA was carried out as follows. First, as shown in the below reaction formula (IV), 4.2 g of anhydrous diglycol acid was taken in a round-bottom flask, and 40 ml of dichloromethane was placed thereto to make a suspension. Subsequently, 7 g of dioctylamine (98% purity) was dissolved in 10 ml of dichloromethane, and was slowly added with a dropping funnel. While stirring at room temperature, anhydrous diglycol acid reacted and it was confirmed that the solution become transparent, and thus reaction completed.

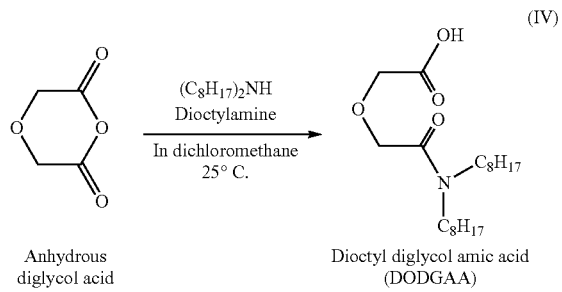

(IV)

Anhydrous diglycol acid → Dioctyl diglycol amic acid (DODGAA)

Next, the above-mentioned solution was washed with water, and the water-soluble impurities were removed. Then, sodium sulfate was added as a dehydrating agent to the solution after water washing. Then, the solution was suction filtered, and subsequently the solvent was evaporated using an evaporator. Then, after recrystallized (three times) using hexane, it was vacuum dried. The recovered amount of the obtained substance was 9.57 g, and the yield based on the above-mentioned anhydrous diglycol acid was 94.3%. Then, the structure of the obtained substance was identified by way of NMR and elemental analysis, upon which it was confirmed to be at least 99% purity DODGAA.

(Extraction of Scandium)

Scandium was extracted by the same method as the Example, except for the extraction agent being DODGAA. The results are shown in FIG. 2. The horizontal axis in FIG. 2 is the pH of the sulfuric acid acidic solution, and the vertical axis is the extraction rate of scandium, calcium or magnesium. In the graph, the diamonds indicate the extraction rate of scandium, the squares indicate the extraction rate of calcium, and the triangles indicate the extraction rate of magnesium.

Results

It has been confirmed that, by using the extraction agent (D2EHAG) of the Example, scandium could be extracted at a high extraction rate in a wide pH range, and could consequently be separated from magnesium and calcium (FIG. 1). On the other hand, with the extraction agent (DODGAA) of the Comparative Example, if the pH was not at least 2.5, a scandium extraction rate enough to satisfy in an industrial sense could not be obtained, and from this it was confirmed that, not only scandium, but also magnesium and calcium, which are impurities, were extracted, and separation was difficult (FIG. 2).

The invention claimed is:

1. A scandium extraction method comprising: subjecting an acidic solution containing calcium, magnesium and scandium to solvent extraction using a scandium extraction agent comprising an amide derivative represented by formula (I), wherein $R^1$ and $R^2$ each represent the same or different linear or branched alkyl groups, and $R^3$ represents hydrogen atom or alkyl group:

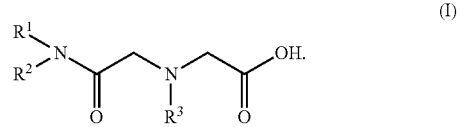

(I)

2. The scandium extraction method according to claim 1, wherein the acidic solution is subjected to the solvent extraction while adjusting the pH of the acidic solution to be in the range of 1 to 4.

3. The scandium extraction method according to claim 1, wherein the acidic solution is a solution formed by mixing sulfuric acid with nickel oxide ore to leach out nickel.

4. The scandium extraction method according to claim 2, wherein the acidic solution is a solution formed by mixing sulfuric acid with nickel oxide ore to leach out nickel.

5. The scandium extraction method according to claim 1, wherein the acidic solution is subjected to the solvent extraction while adjusting the pH of the acidic solution to be in the range of 1.5 to 3.5.

* * * * *